US009700051B2

(12) United States Patent
Brunel et al.

(10) Patent No.: US 9,700,051 B2
(45) Date of Patent: Jul. 11, 2017

(54) USE OF SQUALAMINE OR ANALOGUE AS A DISINFECTING AGENT

(71) Applicants: Jean-Michel Brunel, Marseilles (FR); Didier Raoult, Marseilles (FR); Jean-Marc Rolain, Marseilles (FR)

(72) Inventors: Jean-Michel Brunel, Marseilles (FR); Didier Raoult, Marseilles (FR); Jean-Marc Rolain, Marseilles (FR)

(73) Assignees: ASSISTANCE PUBLIQUE—HOPITAUX DE MARSEILLE, Marseilles (FR); UNIVERSITE D'AIX MARSEILLE, Marseilles (FR); FONDATION MEDITERRANEE INFECTION, Marseilles (FR)

( * ) Notice: Subject to any disclaimer, the term of this patent is extended or adjusted under 35 U.S.C. 154(b) by 0 days.

(21) Appl. No.: 14/371,292

(22) PCT Filed: Jan. 4, 2013

(86) PCT No.: PCT/FR2013/050021
§ 371 (c)(1),
(2) Date: Jul. 9, 2014

(87) PCT Pub. No.: WO2013/104849
PCT Pub. Date: Jul. 18, 2013

(65) Prior Publication Data
US 2015/0005274 A1    Jan. 1, 2015

(30) Foreign Application Priority Data

Jan. 12, 2012 (FR) ..................................... 12 50312

(51) Int. Cl.
*A01N 45/00* (2006.01)
*A01N 49/00* (2006.01)
*A01N 63/02* (2006.01)

(52) U.S. Cl.
CPC ............. *A01N 45/00* (2013.01); *A01N 49/00* (2013.01); *A01N 63/02* (2013.01)

(58) Field of Classification Search
USPC ....................................................... 514/182
IPC ..................................................... A01N 45/00
See application file for complete search history.

(56) References Cited

U.S. PATENT DOCUMENTS 6,350,738 B1 * 2/2002 Savage et al. ................ 514/182
2011/0123624 A1 * 5/2011 Zasloff ........................... 424/489

FOREIGN PATENT DOCUMENTS

WO          2011067501 A1    6/2011
WO    WO 2011/066260    *    6/2011

OTHER PUBLICATIONS

Alhanout et al. (J. Antimicrob Chemother (2010) 65; 1688-1693) Jun. 2011.*
Djouhri Bouktab (Doctorial Thesisis (Dec. 15, 2011) Open Access Theses and Dissertations.*
International Search Report mailed Feb. 25, 2013, corresponding to International Patent Application PCT/FR2013/050021.
Loncle et al.: "Synthesis of new 7-aminosterol squalamine analogues with high antimicrobial activities through a stereoselective titanium reductive amination reaction", Tetrahedron, Elsevier Science Publishers, Amsterdam, NL, vol. 63, No. 52, Nov. 19, 2007, pp. 12968-12974.
Kamel Alhanout et al.:"In vitro antibacterial activity of aminosterols against multidug-resistant bacteria from patients with cystic fibrosis", Journal of Antimicrobial Chemotherapy, Oxford University Press, GB, vol. 64, No. 4, Oct. 1, 2009, pp. 810-814.
Chanaz Salmi et al.:"Efficient preparation of secondary aminoalcohols through a Ti(IV) reductive amination procedure. Application to the synthesis and antibacterial evaluation of new 3beta-N-[hydroxyalkyl]aminosteroid derivatives", Tetrahedron, Elsevier Science Publishers, Amsterdam, NL, vol. 64, No. 19, May 5, 2008, pp. 4453-4459.
Celine Loncle et al.:"Antimicrobial activities of 7-aminosterol squalamine analogues", Letters in Drug Design and Discovery, Bentham Science Publshers, US, vol. 5, No. 6, Sep. 1, 2008, pp. 388-393.
Chanaz Salmi et al.:"Antimicrobial activities of 3-amino- and polyaminosterol analogues of squalamine and trodusquemine", Journal of Enzyme Inhibition and Medicinal Chemistry, Taylor, Reading, GB, vol. 23, No. 6, Dec. 1, 2008, pp. 860-865.
Karen S. Moore et al:"Squalamine: An aminosterol antibiotic from the shark", Proceedings of the National Academy of Sciences, National Academy of Sciences, US, vol. 90, No. 4, Feb. 15, 1993, pp. 1354-1358.

* cited by examiner

*Primary Examiner* — Shirley V Gembeh
(74) *Attorney, Agent, or Firm* — Ladas & Parry LLP

(57) ABSTRACT

The present invention relates to the use of a compound chosen from squalamine and a squalamine-analog aminosteroid compound as agent for disinfecting an inert material object, in particular for the pre-disinfection of medical, dental, diagnostic or surgical equipment.
The present invention also provides an aqueous or water-soluble disinfecting composition beneficial for a use according to the invention, characterized in that as disinfecting active compound it comprises a said antibacterial and anti-fungal compound selected from squalamine and a said squalamine-analog aminosteroid compound and suitable excipients for a water-soluble or aqueous formulation.

16 Claims, 2 Drawing Sheets

USE OF SQUALAMINE OR ANALOGUE AS A DISINFECTING AGENT

Figure 1:
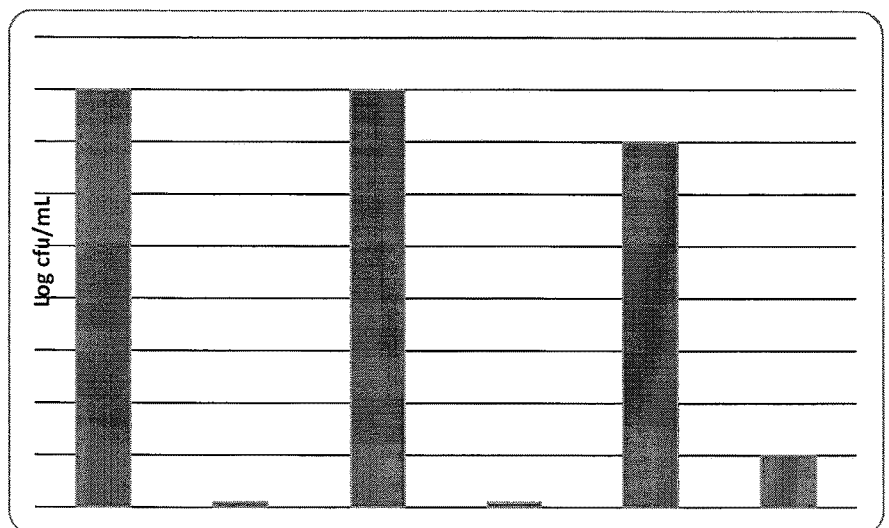

This application is a 371 of PCT/FR2013/050021, filed on Jan. 4, 2013, which claims priority to French Application No. 1250312, filed Jan. 12, 2012.

The present invention concerns a disinfecting agent composition useful in particular for the disinfection of inert (or inanimate) material objects.

By "inert material object" is meant herein an object in inert materials i.e. non-living or non-biological material or not originating from living or biological material.

At the current time, this type of disinfection is performed either by sterilising heat treatment in an autoclave, or by washing or soaking with or in solutions of agents qualified as disinfectants.

A disinfecting agent is a chemical product which kills or inactivates microorganisms such as bacteria, viruses and protozoa. However, unlike an antiseptic agent which is intended to be applied to a human or animal body, or an antibiotic agent which is intended to be administered inside a human or animal body, a disinfectant agent is used to disinfect inert objects. There is a major difference between first an antibiotic activity (direct action on microorganisms and used in man inside the body) or antiseptic activity (destruction of microorganisms on the outer surfaces of the body, in particular living tissue, skin, mucosa), and secondly a disinfecting activity (destruction of microorganisms on inert objects). In practice the antibiotic or antiseptic activity of a chemical substance concerns the action on relatively reduced concentrations of bacteria which can be used in or on man inside or outside the body and must therefore have acceptable toxicity. Some of these antibiotics can be formulated for use as antiseptics. On the other hand, antiseptic or antibiotic agents cannot be used as disinfectants since the antibacterial and antifungal properties required for a disinfecting agent are much more drastic, the concentrations of bacteria to be killed being much higher, meaning that they cannot be used as medicinal products in particular on account of their toxicity.

In everyday language the term "disinfectant" often includes both disinfectants in the strict sense and antiseptics which may lead to confusion. In addition the term "antibacterial" is often misused as a synonym of antiseptic or disinfectant for commercial purposes to highlight the sterilising property of a product, without however heeding the medical specifications for a disinfectant or antiseptic in their strict sense.

Disinfecting agents in their strict sense form one of the four groups (disinfectants, protective products, anti-parasitic products, other products) of Biocides in the meaning of Directive 98/8/CE of the European Parliament and Council of 16 Feb. 1998 concerning the placing of biocidal products on the market. The disinfectants according to the present invention therefore have a precise denomination and a specific European legal status: they are neither antibiotics in the strict sense nor antiseptics.

There are European standards, EN 1040 (for bacteria) and EN 1275 (for yeasts) to qualify a chemical compound as chemical disinfecting agent for use in the pharmaceutical, medical, dental, veterinary, agri-food and industrial sectors, and for domestic or community use. According to the standards in force a disinfecting agent must kill 99.999% of targeted germs i.e. a 5-log reduction using an inoculum of $10^8$ cfu/ml gram$^+$ and gram$^-$ bacteria *S. Aureus* and *P. aeruginosa*, and 99.99% of fungi i.e. a 4-log reduction using an inoculum of $10^8$ cfu/ml yeast (*A. niger* and *C. albicans*).

At the current time in the medical sector, and in particular for cleaning and pre-disinfecting medical instruments, use is made of solutions of disinfecting agents such as alcohol, acid or oxidizing compounds in particular acid glutaraldehyde, ethyl or isopropyl alcohol, sodium hypochlorite.

More particularly, in the case of cystic fibrosis which is a genetic disease characterized by recurrent lung infection, the treatment of this disease requires aerosol antibiotic therapy using nebulizers (1-4). However, on account of the repeated use of these devices, potentially pathogenic germs are frequently found in the nebulizer equipment and this microbial contamination may be the cause of patient re-infection and treatment failure (5-7). Therefore at the present time the cleaning and disinfection of nebulizing equipment are recommended (8). Disinfection can be obtained for example by soaking in solutions containing acetic acid (2%) or in boiling water (9-10). Other methods include soaking in ethanol (70%) or isopropyl alcohol (90%) for 5 minutes, rinsing with tap water followed by air drying (18-19). Sodium hypochlorite has also been recommended but with standards varying from one country to another (11-12). For example, the French association for combating cystic fibrosis recommends the use of sodium hypochlorite solution with 0.08% active chlorine for 15 to 30 minutes, whilst the American foundation recommends soaking of infected equipment in a solution with 0.13% active chlorine for 3 minutes. In 2001, Rosenfield et al. (18) were the first to study nebulizer contamination with a mixture of strains of *S. aureus* and *P. aeruginosa*, by using tap water for cleaning at 35° C. for 30 s followed by drying at ambient temperature. In 2006, a study (20) on the cleaning of ultrasonic nebulizers performed by patients indicated that those who carried out disinfection of the nebulizer with sodium hypochlorite (100 ppm) for 1 hour once a day after use, were less infected than the nebulizers disinfected after a waiting time of 24 hours. More recently Reychler et al. (12,18) compared the in vitro efficacy of numerous commercial disinfectants against numerous Gram positive and Gram negative bacteria, including sodium hypochlorite, 3.5% acetic acid, 0.5% Hexanios, washing-up detergent (0.5%) for 20 minutes and washer (dishwasher) with marked variations regarding the efficacy of these methodologies depending on the bacterial strains under consideration. Also, Monforte et al. (7) have shown that proper disinfection could entail washing of the nebulizer in soapy water after use of the equipment and soaking of this equipment in 1% solution of sodium hypochlorite up until the following use. By following this protocol only 12.5% of patient nebulizers were contaminated whilst 60% were contaminated after following other disinfecting routes. Additionally, the type and quality of water sources used for rinsing nebulizers are variable (demineralised water, tap water, sterile water) possibly leading to results of greater or lesser success. The cumbersome nature of these methods soon becomes apparent since patients use this equipment daily. Also these patients are very largely dependent on their families, in particular their children for everything related to care and maintenance of the equipment; the time to be devoted to mere cleaning of nebulizers for example amounts to a major drawback.

Also, these disinfecting agents are not satisfactory for the following additional reasons.

Some agents such as acid glutaraldehyde are not devoid of effects on equipment in plastic or treated metal material since they may lead to corrosion or degradation.

Also from an ecological viewpoint, one of the major problems is that these disinfecting agents after use are poured into urban wastewater networks even though they represent high quantities of corrosive and/or toxic products that are discharged into wastewater networks degrading piping and increasing the difficulty of controlling biological treatment in downstream treatment stations. Another problem related to toxicity is the relative hazardous nature of the handling of these products by users.

A further problem with disinfecting agents is that they may induce microorganism resistance or a relatively limited spectrum of antibacterial or antifungal action, in the same way as is known in therapy with antibiotic medications or antiseptics.

Finally, *A. Niger* is a filamentous fungus which forms spores that are difficult to eliminate. At the current time, treatment by disinfection with acid glutaraldehyde (0.5%) or alkaline glutaraldehyde can only obtain a 1-log reduction in the number of spores of *A. Niger* and within a time of 100 minutes (23,24).

It is the objective of the present invention to provide a disinfecting agent that is simple, effective, quick-acting, non-hazardous and practical to use for patient comfort and the comfort of patients' families.

More particularly one objective of the present invention is therefore to produce a novel less toxic disinfecting agent that can be recycled after use in wastewater networks without causing any ecological problem and which has a broad spectrum of action without inducing resistance.

A further objective is to provide a disinfecting agent which also kills fungus spores.

A further objective of the invention is to provide a disinfecting agent which has the fastest possible destructive action, in particular within less than 8H and in the form of an aqueous composition.

For this purpose the subject of the present invention is the use of a compound selected from among squalamine and a squalamine-analogue aminosteroid compound as agent to disinfect an inert material object, the said compound being formulated in the form of an aqueous or water-soluble composition.

The present invention also provides an aqueous or water-soluble disinfecting composition useful for a use of the invention, characterized in that as active disinfecting compound it comprises a said compound selected from among squalamine and a said antibacterial and antifungal squalamine-analogue aminosteroid compound with suitable excipients for a water-soluble or aqueous formulation.

By "squalamine-analogue aminosteroid compound" is meant herein an antibacterial and antifungal compound of formula I below.

Squalamine has been described (13-15, 22) as an antibacterial and antifungal agent for therapeutic use whose mode of action is original in that it acts as a detergent, hence it has a resulting broad spectrum of activity and especially action against multi-resistant bacteria and does not induce bacterial resistance. It has been described in WO 20011/067501 that squalamine and its aminosteroid analogues have antibiotic, antibacterial activity in topical application in the form of a lipophilic formulation, in particular an ointment, without cutaneous toxicity and without induced resistance on account of a mechanism of action differing from that of antibiotics, at concentrations of 0.5 to 5 mg/ml and allowing a 4-log reduction of a $10^6$ cfu/ml concentration of *S. aureus* within 24 hours and a 5-log reduction within 48 hours. In addition an in vitro antifungal action has been described at squalamine concentrations of 4-16 ring/l allowing a 4-log reduction of a $10^6$ concentration of *A. niger* within 24 hours.

Such results do not qualify squalamine and its aminosteroid analogues as disinfecting agent in accordance with the objectives of the invention, namely to eradicate much higher quantities of microorganisms while being in the form of an aqueous solution and at concentrations which do not induce cutaneous toxicity.

As mentioned above, in standardised in vitro tests the following reductions must be obtained with a disinfecting agent:
   a 5-log reduction for a concentration of *S. aureus* and *P. aeruginosae* of $10^8$ cfu/ml; and
   a 4-log reduction for a concentration of *A. niger* and *C. albicans* of $10^8$ cfu/ml.

In addition, according to the invention, it was sought to produce a disinfecting agent in formulations in an aqueous medium at concentrations not inducing cutaneous toxicity in an aqueous medium.

The inventors have found that squalamine and its aminosteroid analogues meet these criteria at concentrations in an aqueous solution of 2 000 ring/l and that at these concentrations they do not cause cutaneous toxicity and in addition they allow a 4-log reduction of spores.

Finally it was observed that squalamine and its said analogues do not induce any degradation of the equipment treated and/or in contact with the product.

Although squalamine and its aminosteroid analogues were capable in topical application in the form of a lipophilic composition to reduce a concentration of $10^6$ *S aureus* by 4-log in 24 hours without inducing resistance, it was not at all obvious that these compounds could obtain a 5-log reduction in less than 1 hour of a $10^8$ concentration of *S. aureus* or *P. aeruginosa*, or 4-log reduction in less than 8 hours of a $10^8$ concentration of *C. albicans* or *A. niger* (including eradication of spores with regard to *A. niger*). The microorganism concentrations involved for disinfection are higher (100 times) and the disinfectant effect must be obtained more rapidly. The other antibiotics used in man do not have this capability, nor do most of the antiseptics.

In addition, it was not obvious either that it would be possible to produce aqueous or water-soluble compositions such as water-soluble tablets able to have this desired efficacy in order to qualify as disinfectant.

More particularly, the present invention concerns compositions of disinfecting agents useful in particular for the disinfection of objects used in the food, home, transport sectors and in medical sectors in particular pharmaceutical, diagnostic, dental or surgical.

Particular mention can be of:
   food utensils in communities in particular for feeding of infants such as feeding bottles, teats, soothers, . . .
   surgical instruments such as scalpels, surgical prostheses, pins, . . .
   medical devices such as eye contact lenses and endoscopic devices such as probes, endoscopes, respiratory masks, . . .
   devices for administering pharmaceutical compositions such as nebulizers.

The objects concerned are more particularly rigid objects in plastic polymer material, inorganic or mineral material, in particular in steel or metal, or in composite material.

The transport sector can also be cited, in particular stretchers and inner claddings of vehicles, ambulances in particular, or the home or transport sectors for domestic or communal use in particular home objects such as furniture and fixtures such as floors, walls, water pipes, seating, door handles, stretchers.

The method of the invention is more particularly advantageous for equipment in plastic materials which cannot be sterilised by heat treatment in an autoclave and/or metal materials which corrode in an acid or oxidizing medium.

More particularly a said compound and a said composition of the invention are capable of killing in vitro:

a) at least 99.999% of pathogenic bacteria *S. aureus* and *P. aeruginosa* in a suspension containing a $10^8$ cfu/ml concentration of said bacteria at 20° C., in particular in less than 60 minutes; and b) at least 99.990% of pathogenic yeasts *C. albicans* and *A. niger* in a suspension containing a concentration of at least $10^7$ cfu/ml of said yeasts at 20° C., in particular in less than 60 minutes.

Characteristics a) and b) correspond to the criteria required by European standards EN 1040 (for bacteria) and respectively EN 1275 (for yeasts) for a chemical disinfecting agent used in the pharmaceutical, medical, veterinary, agri-food, industrial sectors and for domestic or communal use.

Herein the characteristics a) and b) are obtained with concentrations of the said compound of squalamine an aminosteroid analogue of at least 0.3 mM (0.2 g/l) for characteristic a), and at least 3.2 mM (2 g/l) for characteristic b).

More particularly for use according to the invention the said object is placed in contact with an aqueous composition of the said compound of squalamine and aminosteroid analogue.

Further particularly the said object is soaked in the said aqueous solution or a said aqueous composition is applied to the said object.

The said aqueous composition may be contained in a substrate, particularly a gel or wipe capable of releasing the said composition onto the said object when the said substrate is contacted therewith and in particular is moved over the said object.

Still further particularly the said compound is used in the form of an aqueous solution at a concentration of at least 3 mM, preferably at 3 to 8 mM (about 2 to 5 g/l).

Aqueous solutions of said compounds at the above concentrations allow the disinfecting of a said object infected with pathogenic bacteria and/or pathogenic yeasts by killing on the said object:

i) at least 99.999% of pathogenic bacteria *S. aureus* and *P. aeruginosa* on a said object in less than 20 minutes at 20° C.; and ii) at least 99.990% of pathogenic yeasts *C. albicans* and *A. niger*, including spores, in less than 6 hours at 20° C.

Further particularly a solid water-soluble composition is diluted in an aqueous solution, the composition preferably being in powder or tablet form containing a said compound at a concentration of at least 2.5% by weight, the said composition being soluble in an aqueous solution.

Still further particularly the said compound is squalamine of following formula Ia:

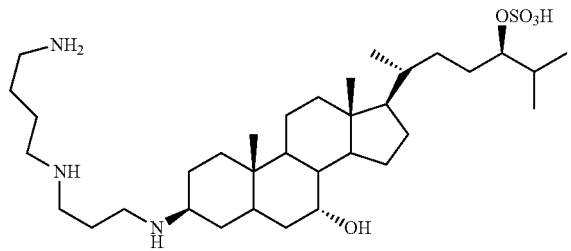

Yet further particularly, the said squalamine-analogue aminosteroid compound meets a general formula comprising a backbone of formula (I) below on which at least 1 polyamine chain —NHR is grafted, R being an optionally substituted hydrocarbon chain comprising at least one —$NH_2$ group: (I)

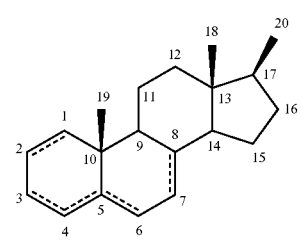

where:

either all the bonds lined with a dotted line between the carbons at positions 7-8, 5-6, 4-5, and 3-4 represent a single bond, the backbone being that of a 10, 13, 17 trimethyl cholestane;

or one of the bonds lined with a dotted line between the carbons at positions 7-8, 5-6, 4-5 and 3-4 represents a double bond and the other bonds lined with a dotted line are single bonds, the backbone being that of a 10, 13, 17 trimethyl cholestene.

Furthermore particularly, the said compound meets a general formula comprising a said backbone of formula (I) comprising:

a) at least 1-NHR chain on one of the carbons at positions 3, 7 and 20, and R represents —$[(CH_2)n\text{-}(NR_1)_k—(CH_2)_m]_p$—$NH_2$ where:

n and m are integers, the same or different from 1 to 7;

k=0 or 1;

p is an integer of 1 to 4; and $R_1$ is selected from among H, a C1 to C8 alkyl, in particular C1 to C3 alkyl, an optionally substituted phenyl and a —COOalk group, alk being a C1 to C3 alkyl;

preferably with:

if k=0, then p=1 or if k=1, then p=2; and if the said compound comprises a single —NHR chain, this is preferably grafted at position 3 or 7; and b) the other carbons of the said backbone comprising a radical $R_0$ the same or different selected from among H, OH, $NH_2$, SH, and $R_1$, preferably $R_0$ being H or OH but only a single $R_0$ represents OH.

Still further particularly, the said aminosteroid compound meets one of the following general formulas IIa, IIb, IIc or IId wherein R represents —$[(CH_2)_n—(NR_1)_k—(CH_2)_m]_p$—$NH_2$, n, m, p, k and $R_1$ having the denotations given above, and preferably R is selected from among: —$(CH_2)_{n_1}$-$NH_2$ wherein $n_1$=2 to 14, and —$(CH_2)_3$—NH—$(CH_2)_3$—NH—$(CH_2)_3$—$NH_2$:

IIa

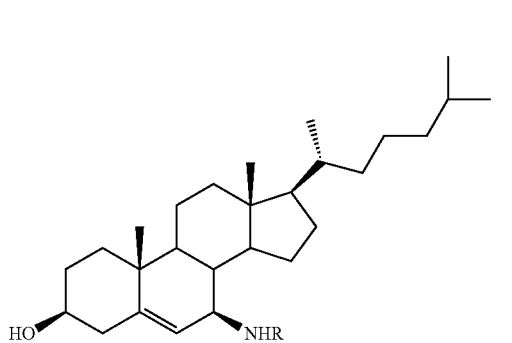
Ou

IIb

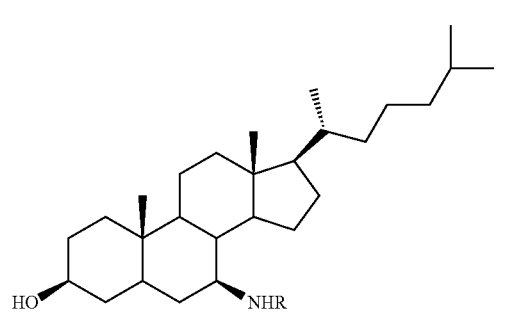
Ou

IIc

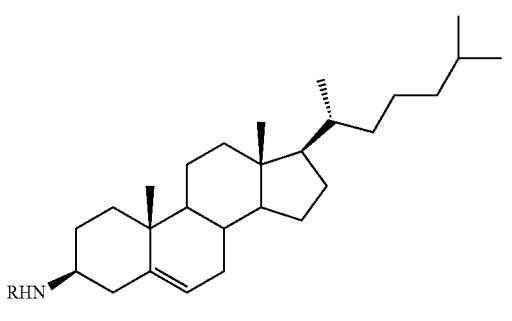
Or

IId

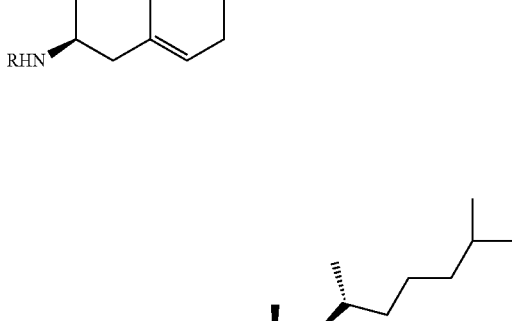

Still further particularly the said compound is an aminosteril called ASD 2 meeting the following general formula II-1:

II-1

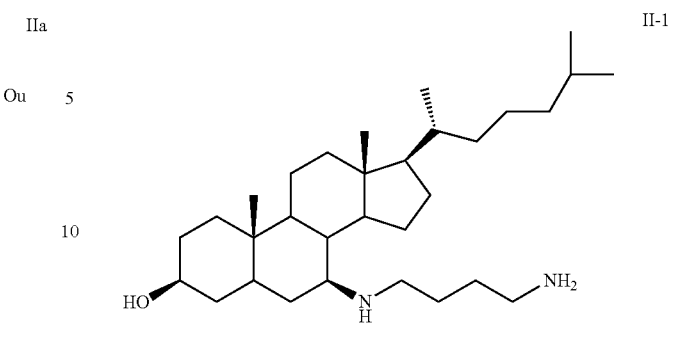

Other said suitable compounds meet the general formula formed by a said backbone of formula (I) having:

a) 2 identical —NHR chains on the carbons at positions 3 and 20 respectively, and R is —[(CH$_2$)n-(NR$_1$)$_k$—(CH$_2$)$_m$]$_p$—NH$_2$ where:

n and m are integers, the same or different, from 1 to 7;

k=0 or 1;

p is an integer from 1 to 4;

R$_1$ being selected from among H, a C1 to C8 alkyl, in particular C1 to C3 alkyl, an optionally substituted phenyl and a —COOalk group, alk being a C1 to C3 alkyl;

wherein preferably if k=0, then p=1, or if k=1, then p=2; and b) the other carbons of the said backbone of formula (I) comprise a radical R$_0$ the same or different selected from among H, NH$_2$, SH or R$_1$, preferably R$_0$ being H or OH but with only a single R$_0$ being OH.

Still further particularly, the said compound meets the following general formulas IIIc or IIIb, wherein R represents —[(CH$_2$)$_n$—(NR$_1$)$_k$—(CH$_2$)$_m$]$_p$—NH$_2$, and preferably R is selected from among —(CH$_2$)$_n$—NH$_2$ where n=2 to 14, and —(CH$_2$)$_3$—NH—(CH$_2$)$_3$—NH—(CH$_2$)$_3$—NH$_2$:

IIIa

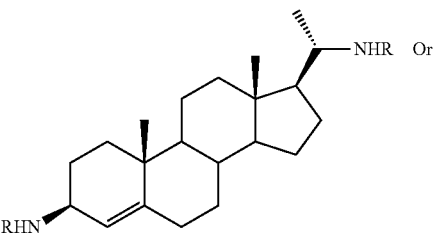

IIIb

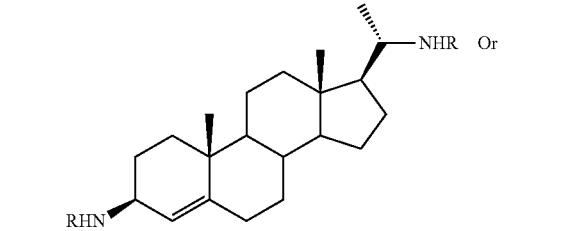

Still further particularly, the said aminosteroid compound meets following formula III-1:

III-1

[Chemical structure diagram of squalamine showing steroid backbone with HN, NH₂, H₂N substituents]

Still further particularly, a composition of the invention has a concentration of 0.5 to 5%, preferably at least 2.5% by weight of said squalamine compound or said squalamine-analogue aminosteroid compound in the form of a water-soluble salt.

Still further particularly a composition of the invention is in the form of an aqueous solution or solid water-soluble tablet or water-soluble powder, the said excipients preferably being selected from among microcrystalline cellulose, lactose, starch, croscarmellose sodium, colloidal silica and magnesium stearate.

Still further particularly the said antibacterial squalamine compound or said squalamine-analogue aminosteroid compound is in the form of a water-soluble salt, preferably in the form of a hydrochloride, hydrobromide, triflate, phosphate, lactate or succinate salt.

Still further particularly the said material object is equipment for food, medical, dental, pharmaceutical, diagnostic or surgical use.

Other characteristics and advantages of the present invention will become better apparent on reading the following description given as a non-limiting illustration with reference to the appended drawings in which:

FIG. 1 gives the disinfection results for 1-hour treatment on infected equipment, as per standards FR-EN1040 and FR-EN1275, with squalamine concentrations of 0.5 g/l to treat *S. aureus* and *P. aeruginosa* and 2 g/l to treat *C. albicans* and *A. niger;*

Figure 1A:
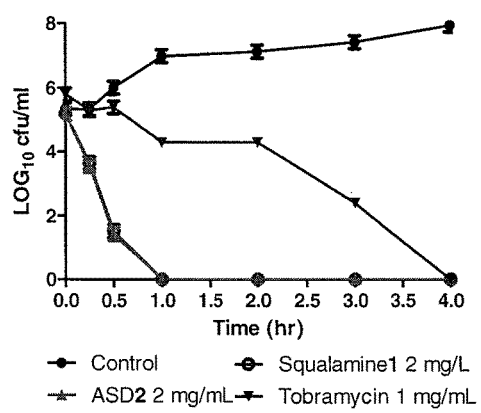
Figure 1B:
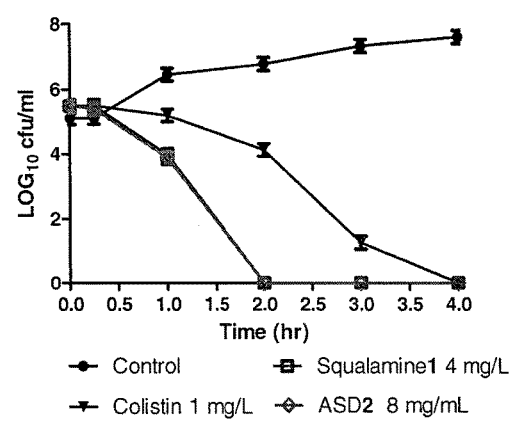
Figure 2A:
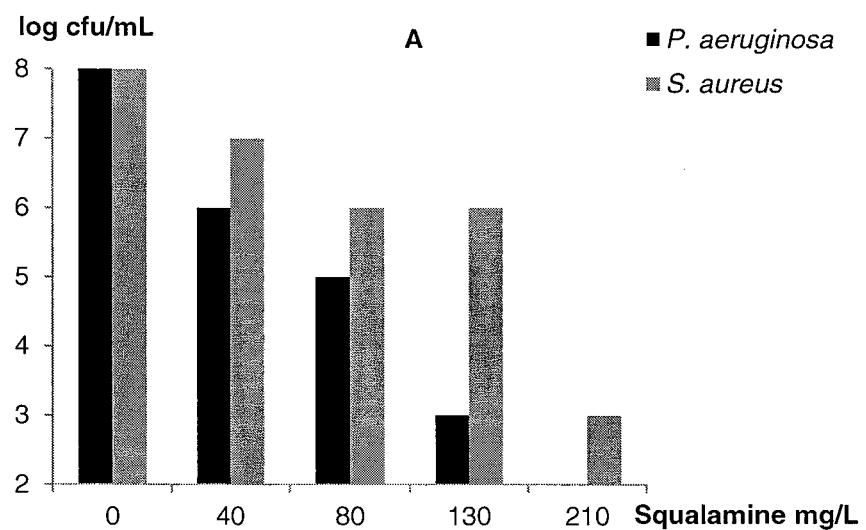
Figure 2B:
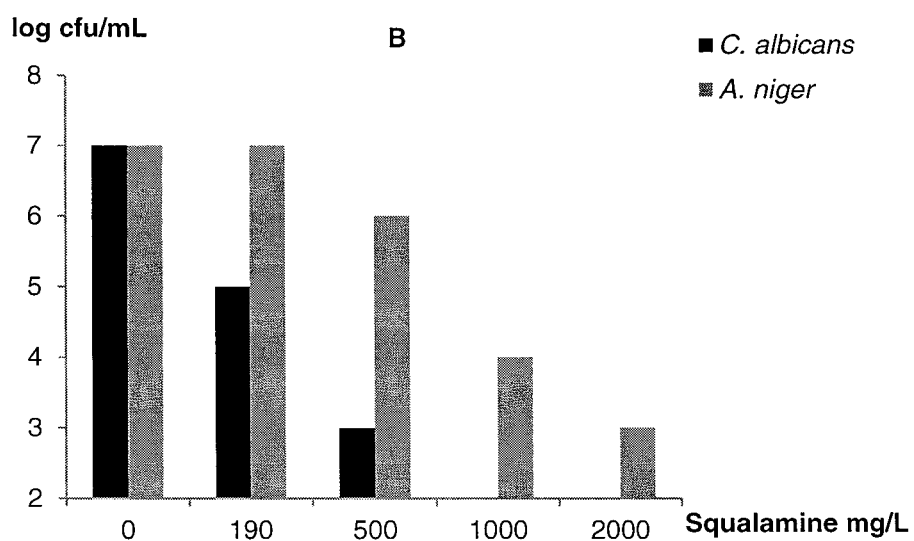

FIGS. 1A and 1B give the Time Kill curves for squalamine and the aminosteroid derivative ASD 2 on *S. aureus* (FIG. 1A) and *P. aeruginosa* (FIG. 1B); and FIGS. 2A and 2B give the disinfection results of a nebulizer with different concentrations of squalamine on bacteria (FIG. 2A) and fungi (FIG. 2B).

In the different tests below the strains used were *Pseudomonas aeruginosa* DSM 939 (ATCC 15442), *Staphylococcus aureus* DSM 799 (ATCC 6538), *Candida* albicans DSM 1386 (ATCC 10231) and *Aspergillus niger* ATCC 16404.

1) Test on disinfecting antibacterial action as per standard FR-EN 1040.

1.1) Protocol.

The microbial contamination of nebulizers was obtained in vitro by soaking the inner part of nebulizers (Pari LC, SPRINT SP, Pari, Germany) in a bacterial suspension prepared in Mueller Hinton broth containing $1 \cdot 10^8$ to $5 \cdot 10^8$ cfu/mL of bacteria. Disinfection was performed by soaking this same part in a solution of sterile water containing squalamine for 1 h at a determined concentration of 0.5 g/L for the bacteria under consideration (*S. aureus* or *P. aeruginosa*). The nebulizer was then rinsed with two successive sterile water solutions. The bacterial count was performed on the second wash bath on Tryptone Soya Agar (24 h).

1.2) Result.

It was found that the aqueous solution of squalamine or ASD 2 used at 0.5 g/l obtains an 8-log reduction of viable cells of *S. aureus, P. aeruginosa* within 1 hour which is more efficient than recommended by the standard which specifies a 5-log reduction in 1 hour (Figure).

2) Test on Disinfecting Antifungal Activity as Per Standard FR-EN 1275.

2.1) Protocol.

Nebulizer contamination with fungi was obtained in vitro by soaking the inner part of nebulizers (Pari LC, SPRINT SP, Pari, Germany) in $1 \cdot 10^7$ fungi suspension at $5 \cdot 10^7$ cfu/mL prepared in Sabouraud broth. After incubation the nebulizer was soaked in sterile water containing squalamine at the determined concentrations in relation to the fungal strains under consideration (i.e. 0.5 g/L for *C. albicans* (1 hour soaking) and 2 g/l for *A. niger* (6 h soaking). The nebulizer was then rinsed with two successive solutions of sterile water. The fungal count was performed on the second wash bath. The count of fungal colonies was performed on malt extract agar-agar (48 h).

2.2) Result.

It was ascertained that the aqueous solution of squalamine or ASD 2 used 0.5 g/l allowed a 6-log reduction in viable cells of *C. albicans* and *A. niger* in 1 h, which fully tallies with the recommendations set by the standard (minimum 4-log [Figure]). However for *A. Niger*, on account of the presence of spores, a concentration of 2 g/l was needed to obtain a 4-log reduction of viable spore cells in 6 hours. A higher concentration would allow this time of fungicidal action to be further reduced if desired.

3) Water-Soluble Composition of Squalamine and ASD 2.

A formulation of squalamine in the form of water-soluble tablets was prepared as follows. A batch of 20 g was prepared; the mixture was mixed in a Turbula Tapent T 20 mixer, Switzerland. The tablets were formed in a press of type Korsch Erwika Tape EKO, Germany. The raw materials were initially sieved. The squalamine (0.5 g) was mixed with microcrystalline cellulose (7.2 g), lactose (10 g), starch (1.4 g), croscarmellose sodium (0.6 g) and colloidal silica (0.04 g). Sieved magnesium stearate was subsequently added and mixed. The final mixture was compressed on an alternating press equipped with 8.0 mm pistons. The excipients used had a specifically adapted particle size (50.0 μm) to obtain compression. The water-soluble tablets obtained containing 2.5% of compound were then stored in a low density polyethylene bottle.

The disinfection experiments were conducted less than 10 days after manufacture of the squalamine tablets. We were nevertheless able to demonstrate the stability of these tablets since more than one year after their manufacture their activity remained unchanged.

4) Disinfectant Treatment of a Nebulizer with an Aqueous Solution of Water-Soluble Composition of Squalamine and ASD 2.

The bacterial contamination of nebulizers is a major problem for patients suffering from cystic fibrosis leading to reduced performance of nebulizers and an increased risk of patient re-infection with polluting bacteria.

The inventors validated the use of squalamine and ASD 2 in the following in vitro model of nebulizer disinfection.

4.1) Material and Method.

Nebulizers of Pari LC type were infected with bacteria (*S. aureus* and *P. aeruginosa*) via a suspension calibrated at $10^8$ cfu/ml, and with fungi (*C. albicans* and *A. niger*) via a suspension calibrated at $10^7$ cfu/ml. These nebulizers were then disinfected by soaking in a squalamine solution for 20 min, Glutaraldehyde and korsolex (peracetic acid) being used as inhibition control.

The microbial contamination of the nebulizer was obtained in vitro by soaking the inner part of the nebulizer (Pari LC, SPRINT SP, Pari, Germany) in a bacterial suspension prepared in Mueller Hinton broth containing $1 \cdot 10^8$ to $5 \cdot 10^8$ cfu/ml of bacteria (NF EN 1040, 1997) for 20 minutes. Disinfection was obtained by soaking this same part in a sterile water solution containing squalamine or ASD 2 for 2 minutes at the determined concentration in relation to the bacteria under consideration. For the fungi, suspensions of $1 \cdot 10^7$ to $5 \cdot 10^7$ cfu/ml (NF EN 1275, 1997) were prepared in Sabouraud broth and after incubation the nebulizer was soaked in sterile water containing squalamine or ASD 2. The nebulizer was then rinsed with two successive solutions of sterile water. The bacterial or fungal count was performed on the second wash bath. The counting of bacterial or fungal colonies was conducted on Tryptone Soya Agar for 24 hours for bacterial growth and on malt extract agar-agar for fungi at 37° C. for 48 hours.

The bactericidal and fungicidal test was performed three times in independent experiments and each bacterium and mould was evaluated separately. The concentration of squalamine and ASD 2 was increased until the required bactericidal and fungicidal activity was obtained. The disinfection time was set at 20 minutes for the first case and subsequently extended to 6 hours for *A. Niger*.

4.2) Result.

It was found that the aqueous solution of squalamine or ASD 2 used at 0.5 g/l obtains a 5-log reduction in viable cells of *S. aureus, P. aeruginosa* and a 4-log reduction for *C. albicans* in 20 minutes, whilst a concentration of 2 g/l was needed to obtain a 4-log reduction in viable cells of *A. Niger* within 6 hours.

4.2.1) The nebulizers used were infected with different bacterial suspensions (*S. aureus* and *P. aeruginosa*) calibrated at $10^8$ cfu/ml or fungal suspensions (*C. albicans* and *A. niger*) calibrated at $10^7$ cfu/ml. In a preliminary set of experiments, values of Minimum Inhibitory Concentration (MIC) and Time Kill of squalamine and ASD 2 were determined against chosen reference bacteria and fungi (MIC only). The MIC values were 2, 4, 16 and 16 mg/l against *S. aureus, P. aeruginosa, C. albicans* and *A. Niger*, respectively (Table 1 and FIGS. 1A-1B). A time of 20 minutes was defined to carry out nebulizer disinfection using squalamine whilst korsolex PAA and the 2% solution of glutaraldehyde were used for a time of 15 minutes following the manufacturers' instructions to obtain disinfecting properties. At a first attempt, it was able to be shown that the use of a dose of 80 mg/ml squalamine or ASD-2 for 20 minutes leads to a 2- and 3-log reduction for bacteria whilst a 2-log reduction for *C. albicans* was only obtained when using a concentration of squalamine or ASD-2 of 190 mg/ml. At the same time, no significant decrease was noted for *A. Niger*. Nonetheless, squalamine and ASD 2 used at a concentration stronger than 0.5 g/l are capable of obtaining a $5\text{-}\log_{10}$ reduction in viable cells of bacteria such as *S. aureus, P. aeruginosa* and a $4\text{-}\log_{10}$ reduction for fungi such as *C. albicans* with a cycle of 20 min (FIG. 2A). On the other hand, for *A. niger*, the concentration enabling a fungicidal effect to be obtained (i.e. not only fungistatic but additionally with spore eradication) was higher than for the bacteria and over a longer time (2 g/l for 6 hours) (FIG. 2B).

The squalamine tablets therefore exhibited their capability of reducing by 5-log the number of viable bacterial cells after a contact time of 20 minutes, similar to the results obtained under homogenous experimental conditions. It is also noteworthy that these tablets disintegrate in less than 5 minutes in water, indicating easy, non-hazardous handling thereof. An improvement on this tablet model can be obtained by preparing effervescent tablets which ensure faster, homogeneous dispersion of squalamine in the medium.

To conclude, squalamine or an analogue of squalamine appears to be a simple, quick and efficient solution for disinfecting any material which be contaminated.

Within this context, a 5-log reduction of viable bacterial cells and 4-log reduction of viable fungal cells is observed, thereby demonstrating the disinfecting activity of squalamine. A 4-log reduction in the fungal growth of *A. Niger* requires a longer treatment period (6 hours) than for bacteria, conforming to the MIC value of squalamine which was higher for fungi compared with bacteria. However, *A. Niger* is a filamentous fungus which forms spores that are difficult to eliminate and the tested compounds allowed a 4-log reduction also to be obtained in the number of *A. Niger* spores.

TABLE 1

Anti-microbial activities and dose needed to ensure nebulizer disinfection.

| Strains | MIC (mg/l) Squalamine 1 | ASD 2 | Squalamine 1 and ASD 2 (mg/l) |
|---|---|---|---|
| *S. aureus* DSM 799 | 2 | 2 | 210 |
| *P. aeruginosa* DSM 939 | 4 | 8 | 130 |
| *C. albicans* DSM 1386 | 16 | 8 | 500 |
| *A. niger* ATCC 16404 | 16 | 8 | 2000 |

5) Toxicity and Corrosion:

Cutaneous toxicity was examined over a period of 15 days by applying a squalamine ointment onto the backs of shaven mice (batch of 10 mice). No skin lesion, redness or inflammation of any kind was able to be observed. Also the mice did not lose weight and continued to feed and drink in comparable manner to non-treated mice.

Concerning a potential effect on plastic or metallic material, a nebulizer was left for 8 days in a squalamine solution having a concentration of 2 g/L and no deterioration of the metal or plastic (in particular regarding colour and flexibility) was observed.

No cutaneous toxicity was observed and the compounds had no effect on plastic or metal material and did not cause any degradation thereof.

BIBLIOGRAPHY

1. O'Malley C A, VandenBranden S L, Zheng X T, et al. A day in the life of a nebulizer: surveillance for bacterial growth in nebulizer equipment of children with cystic fibrosis in the hospital setting. *Respir Care* 2007; 52: 258-62.
2. Lester M K, Flume P A, Gray S L, et al. Nebulizer use and maintenance by cystic fibrosis patients: a survey study. *Respir Care* 2004; 49: 1504-8.
3. Kesser K C, Geller D E. New aerosol delivery devices for cystic fibrosis. *Respir Care* 2009; 54: 754-67.
4. Borsje P, de Jongste J C, Mouton J W, et al. Aerosol therapy in cystic fibrosis: a survey of 54 CF centers. *Pediatr Pulmonol* 2000; 30: 368-76.

5. Blau H, Mussaffi H, Mei Z M, et al. Microbial contamination of nebulizers in the home treatment of cystic fibrosis. *Child Care Health Dev* 2007; 33: 491-5.
6. Cohen H A, Kahan E, Cohen Z, et al. Microbial colonization of nebulizers used by asthmatic children. *Pediatr Int* 2006; 48: 454-8.
7. Monforte V, Roman A, Gavalda J, et al. Contamination of the nebulization systems used in the prophylaxis with amphotericin B nebulized in lung transplantation. *Transplant Proc* 2005; 37: 4056-8.
8. Saiman L, Siegel J. Infection control in cystic fibrosis. *Clin Microbiol Rev* 2004; 17: 57-71.
9. Jakobsson B M, Onnered A B, Hjelte L, et al. Low bacterial contamination of nebulizers in home treatment of cystic fibrosis patients. *J Hosp Infect* 1997; 36: 201-7.
10. Jakobsson B, Hjelte L, Nystrom B. Low level of bacterial contamination of mist tents used in home treatment of cystic fibrosis patients. *J Hosp Infect* 2000; 44: 37-41.
11. Reychler G, Aarab K, Van O C, et al. In vitro evaluation of efficacy of 5 methods of disinfection on mouthpieces and facemasks contaminated by strains of cystic fibrosis patients. *J Cyst Fibros* 2005; 4: 183-7.
12. Reychler G, Leonard A, Van O C, et al. Impact of hypochlorite-based disinfection on bacterial contamination of cystic fibrosis patients' home-nebulisers. J Hosp Infect 2009; 72: 351-7.
13. Alhanout K, Brunel J M, Raoult D, et al. In vitro antibacterial activity of aminosterols against multidrug-resistant bacteria from patients with cystic fibrosis. J Antimicrob Chemother 2009; 64: 810-4.
14. Alhanout K, Brunel J M, Ranque S, et al. In vitro antifungal activity of aminosterols against moulds isolated from cystic fibrosis patients. J Antimicrob Chemother 2010; 65: 1307-9.
15. Alhanout K, Malesinki S, Vidal N, et al. New insights into the antibacterial mechanism of action of squalamine. J Antimicrob Chemother 2010.
16. Andrews J M. Determination of minimum inhibitory concentrations. J Antimicrob Chemother 2001; 48 Suppl 1: 5-16.
17. Vassal S, Taamma R, Marty N, et al. Microbiologic contamination study of nebulizers after aerosol therapy in patients with cystic fibrosis. Am J Infect Control 2000; 28: 347-51.
18. Rosenfeld M, Joy P, Nguyen C D, et al. Cleaning home nebulizers used by patients with cystic fibrosis: is rinsing with tap water enough? J Hosp Infect 2001; 49: 229-30.
19. Allan J, Cunniffe J G, Edwards C, et al. Nebulizer decontamination. J Hosp Infect 2005; 59: 72-4.
20. Oie S, Makieda D, Ishida S, et al. Microbial contamination of nebulization solution and its measures. Biol Pharm Bull 2006; 29: 503-7.
21. Denton M, Rajgopal A, Mooney L, et al. *Stenotrophomonas maltophilia* contamination of nebulizers used to deliver aerosolized therapy to inpatients with cystic fibrosis. J Hosp Infect 2003; 55: 180-3.
22. Alhanout K, Djouhri L, Vidal N, et al. In vitro activity of aminosterols against yeasts involved in blood stream infections. Med Mycol 2010.
23. Gorman S P, Scott E M, Russell A D. Antimicrobial activity, uses and mechanism of action of glutaraldehyde. J Appl Bacteriol 1980; 48: 161-90.
24. Vizcaino-Alcaide M J, Herruzo-Cabrera R, Fernandez-Acenero M J. Comparison of the disinfectant efficacy of Perasafe and 2% glutaraldehyde in in vitro tests. J Hosp Infect 2003; 53: 124-8.

The invention claimed is:
1. A method of disinfecting an inert material object comprising:
providing an agent for disinfection of the inert material object, said agent being a water-soluble salt of squalamine, or a water-soluble salt of an antibacterial and antifungal squalamine-analogue aminosteroid;
formulating said compound as an aqueous solution, or as a solid, water-soluble composition;
contacting the inert material object with an aqueous solution of the formulated compound; and
wherein said compound is capable of killing in vitro:
a) at least 99.999% of pathogenic bacteria *S. aureus* and *P. aeruginosa* in a suspension containing a concentration of $10^8$ cfu/ml of said bacterium at 20° C.; and
b) at least 99.990% of pathogenic yeasts *C. albicans* and *A. niger* in a suspension containing a concentration of at least $10^7$ cfu/ml of said yeast at 20° C.
2. The method according to claim 1, wherein said inert material object is equipment for food, medical, dental, pharmaceutical, diagnostic, or surgical use.
3. The method according to claim 1, wherein said inert material object is placed in contact with an aqueous composition of squalamine or said aminosteroid analogue compound.
4. The method according to claim 1, wherein said compound is used in the form of an aqueous solution at a concentration of 3 mM to 8 mM.
5. The method according to claim 3, wherein a solid water-soluble composition in powder or tablet form containing the compound at a concentration of at least 2.5% by weight is diluted in an aqueous solution, said composition being soluble in an aqueous solution.
6. The method according to claim 1, wherein said compound is squalamine of formula Ia:

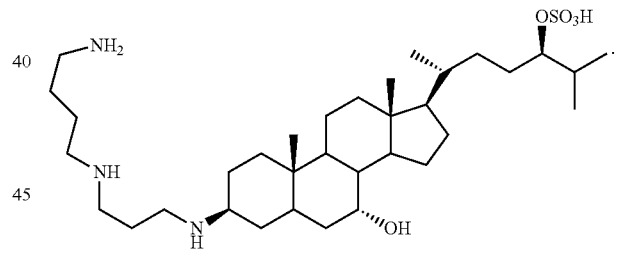

7. The method according to claim 1, wherein said squalamine-analogue aminosteroid compound has a formula comprising a backbone of formula (I) below, on which at least one polyamine-NHR chain is grafted, R being an optionally substituted hydrocarbon chain comprising at least one -$NH_2$ group:

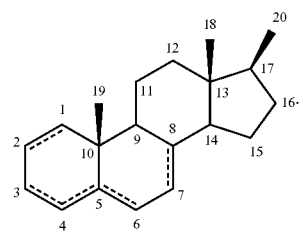

where:
either all the bonds lined with a dotted line between the carbons at positions 7-8, 5-6, 4-5, and 3-4 represent a single bond, the backbone being that of a 10, 13, 17 trimethyl cholestane, or one of the bonds lined with a dotted line between the carbons at positions 7-8, 5-6, 4-5, and 3-4 represents a double bond and the other bonds lined with a dotted line are single bonds, the backbone being that of a 10, 13, 17 trimethyl cholestene.

8. The method according to claim 7, wherein said compound has a formula comprising the backbone of formula (I) comprising:

a) at least 1-NHR chain on one of the carbons at positions 3, 7, and 20, and R is —$[(CH_2)n\text{-}(NR_1)_k\text{—}(CH_2)_m]_p$—$NH_2$ where:
n and m are integers, the same or different, from 1 to 7;
k=0 or 1;
p is an integer from 1 to 4; and
$R_1$ is selected from H, a C1 to C8 alkyl, an optionally substituted phenyl and -COOalk group, alk being a C1 to C3 alkyl; and b) the other carbons of said backbone comprise a radical $R_0$ the same or different selected from H, OH, $NH_2$, SH and $R_1$.

9. The method according to claim 8 wherein:
a) in the formula of R:
if k=0, then p=1, or if k=1, then p=2; and
if said compound comprises a single-NHR chain, this is grafted at position 3 or 7; and
b) the radical $R_0$, on the other carbons of said backbone, is H or OH, but with only one $R_0$ representing OH.

10. The method according to claim 8, wherein said aminosteroid compound has one of the following formulas IIa, IIb, IIc, or IId, wherein R represents —$[(CH_2)_n$—$(NR_1)_k$—$(CH_2)_m]_p$—$NH_2$, where

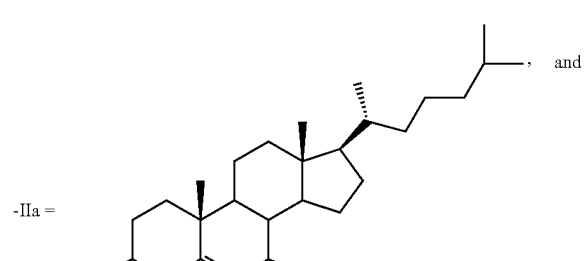

-IIa =

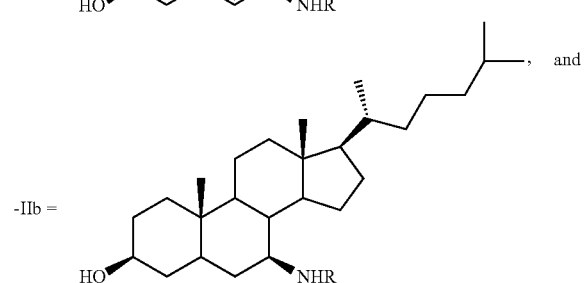

-IIb =

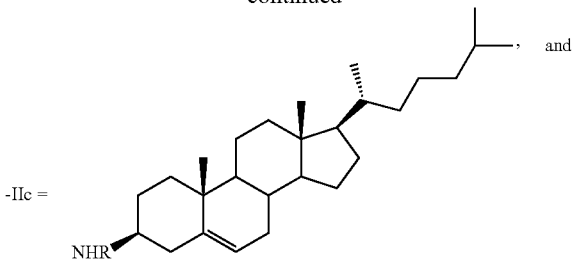

-IIc =

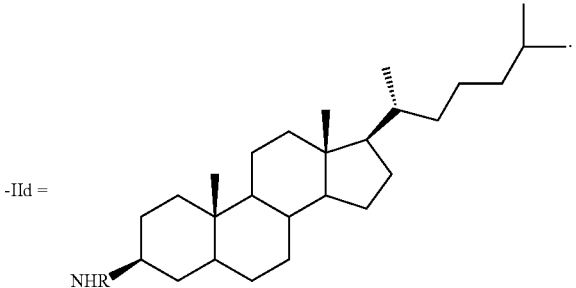

-IId =

11. The method according to claim 10, wherein R is selected from —$(CH_2)n1\text{-}NH_2$, where n1=2 to 14, and —$(CH_2)3\text{-}NH$—$(CH_2)3\text{-}NH$—$(CH_2)3\text{-}NH_2$.

12. The method according to claim 10, wherein said compound has a formula II-1:

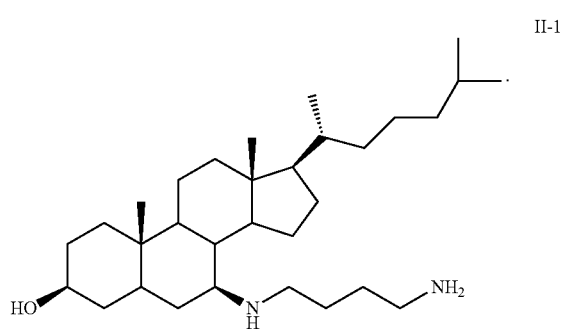 [SMILES: CC(C)CCC[C@@H](C)[C@H]1CCC2C3C(CC[C@@]21C)[C@@]1(C)CC[C@H](O)CC1C[C@@H]3NCCCCN]

II-1

13. A method according to claim 1, wherein said water soluble composition comprises an excipient for formulation in the form of a water-soluble solid tablet or water-soluble powder, said excipient being selected from the group consisting of microcrystalline cellulose, lactose, starch, scroscarmellose sodium, colloidal silica, and magnesium stearate.

14. The method according to claim 1, wherein said water-soluble salt is selected from the group consisting of chlorhydrate, bromhydrate, triflate, phosphate, lactate, and succinate.

15. The method according to claim 1, wherein the inert material object is contacted with an aqueous solution having a concentration of at least 2 g/L of the compound.

16. A method of disinfecting an inert material object comprising:
providing an agent for disinfection of the inert material object, said agent being a water-soluble salt of squalamine, or a water soluble salt of an antibacterial and antifungal squalamine-analogue aminosteroid;
formulating said compound as an aqueous solution, or as a solid, water-soluble composition;
contacting the inert material object with an aqueous solution of the formulated compound; and wherein said compound has a formula II-1:
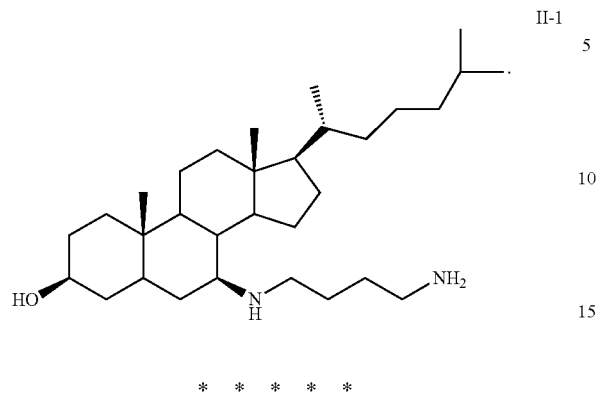
II-1
* * * * *